United States Patent [19]

Pearson et al.

[11] Patent Number: 4,610,877
[45] Date of Patent: Sep. 9, 1986

[54] IMMUNOLOGICAL PREVENTION OF BOAR ODOR IN UNCASTRATED MALE PIGS

[75] Inventors: Albert M. Pearson, Lansing; Roger I. Brooks, East Lansing; Maynard G. Hogberg, Okemos; James J. Pestka, East Lansing; J. Ian Gray, Haslett, all of Mich.

[73] Assignee: Research Corporation, New York, N.Y.

[21] Appl. No.: 662,662

[22] Filed: Oct. 19, 1984

[51] Int. Cl.[4] ................ A01N 37/18; A61K 31/56
[52] U.S. Cl. ................................. 424/88; 514/2; 514/177; 514/182
[58] Field of Search ............... 424/85, 88, 177; 514/177, 182, 2

[56] References Cited

PUBLICATIONS

Shenoy et al., "Acta Endocrinologica", (1982), vol. 100, pp. 131-136.

Primary Examiner—Elbert L. Roberts
Attorney, Agent, or Firm—Scully, Scott, Murphy & Presser

[57] ABSTRACT

The present invention relates to novel immunogens which can be employed in a method for eliminating the offensive odor associated with the preparation of meats derived from uncastrated male pigs. "Boar taint," as the characteristic odor has been termed, can be eliminated, or at least substantially reduced by the administration of novel immunogen compositions which are chemical conjugates formed of certain $C_{19}\Delta^{16}$-steroids and their mixtures with a carrier protein. The immunogens can be administered in conventional forms including a vaccine.

16 Claims, 4 Drawing Figures

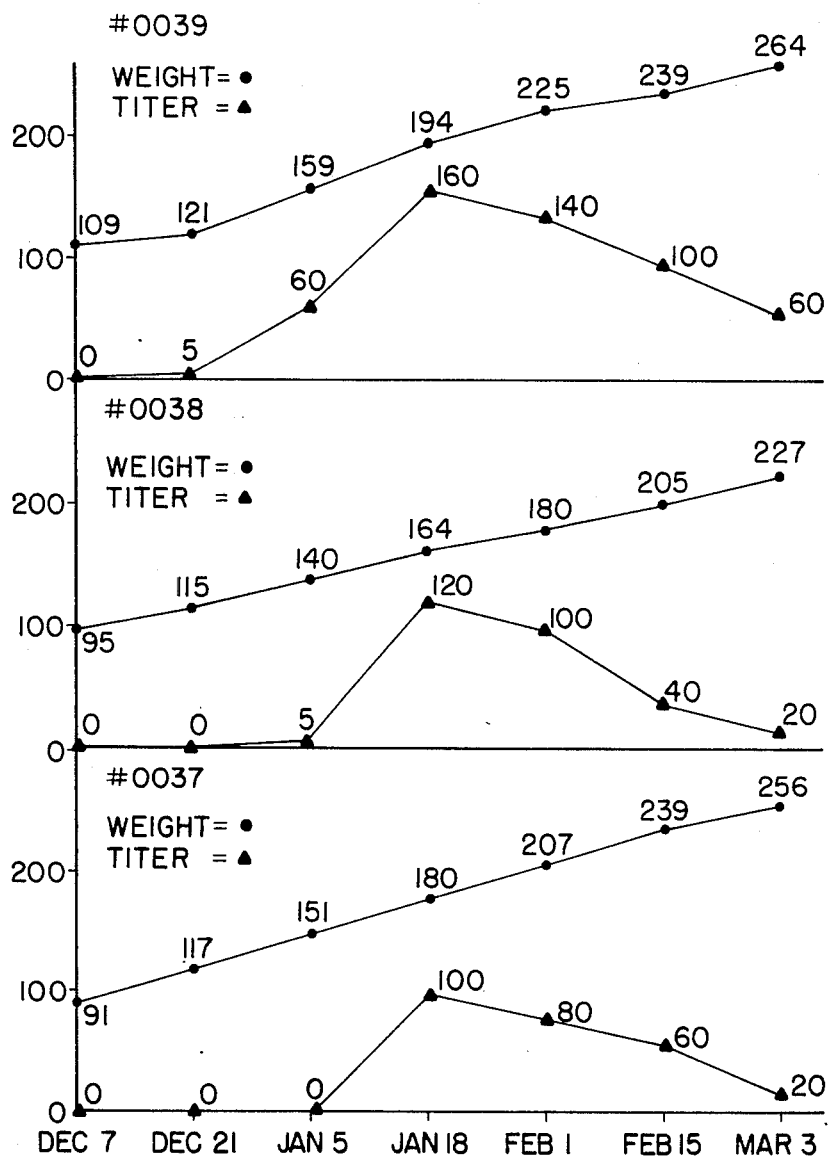

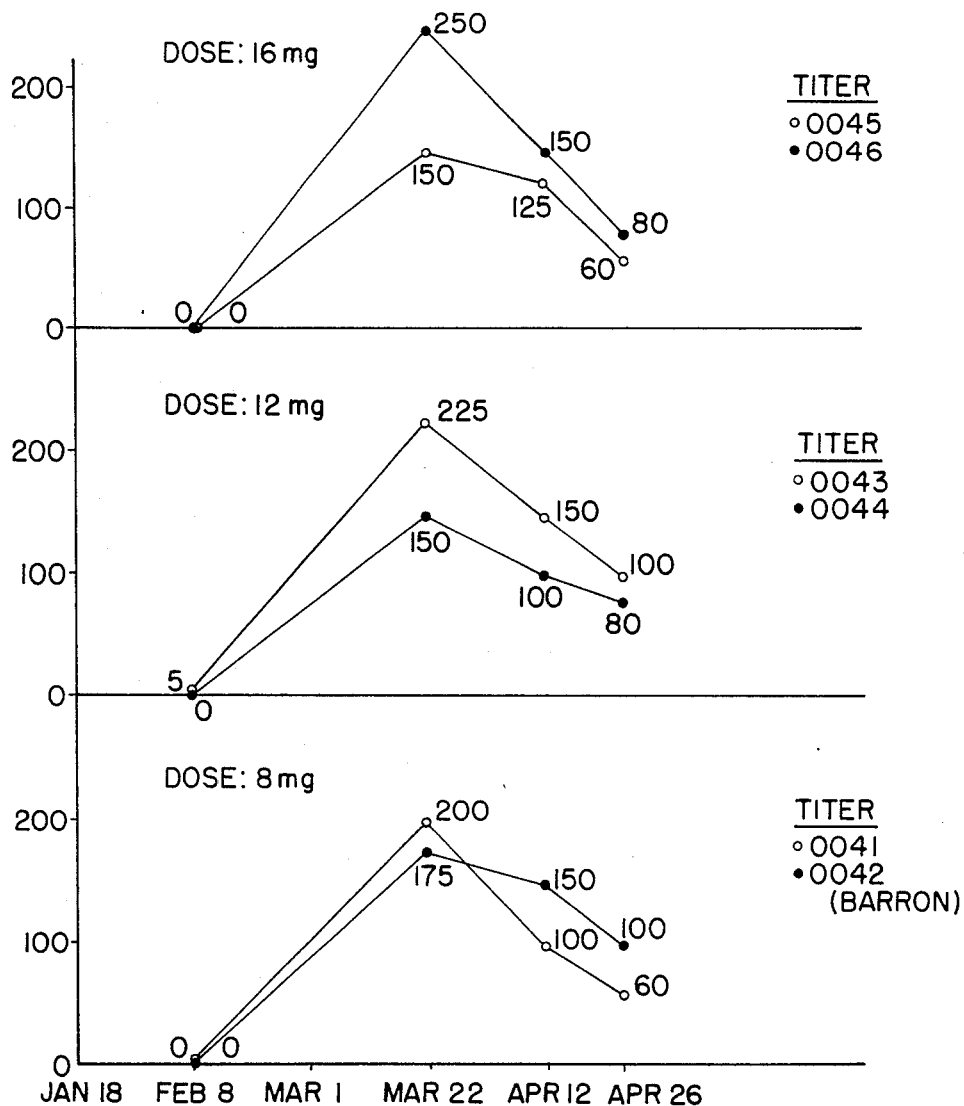
FIG.2. BLOOD TITER LEVELS OF ANTIBODIES TO 5,16-ANDROSTADIEN-3β-ol-BSA IN 6 PIGS INJECTED WITH 8mg, 12mg OR 16mg OF 5,16-ANDROSTADIEN-3β-ol-BSA. EACH PIG RECEIVED AN INITIAL INJECTION AND TWO BOOSTER INJECTIONS AT 21 DAY INTERVALS.

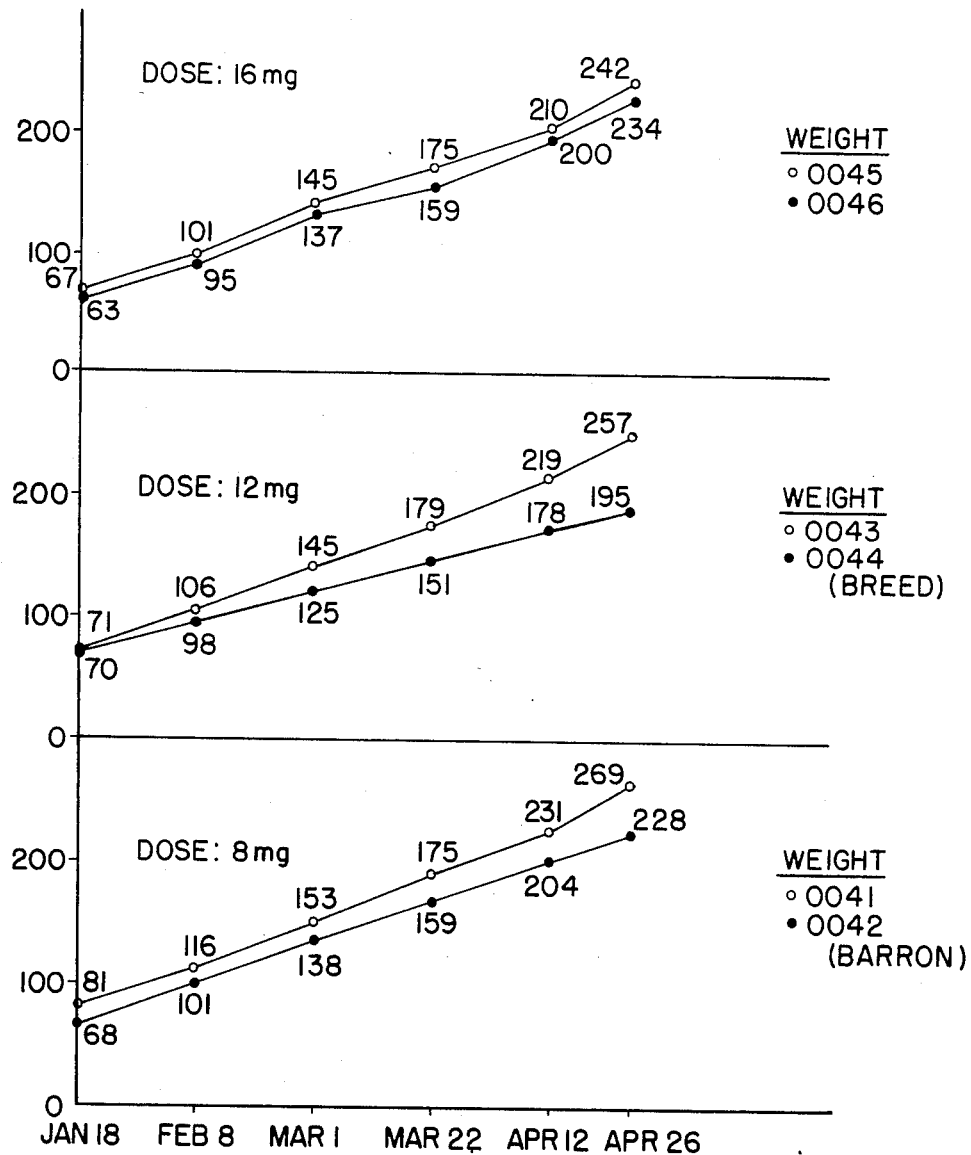
FIG. 3. WEIGHT GAINS OF 6 PIGS INJECTED WITH 8mg, 12mg AND 16mg OF 5,16-ANDROSTADIEN-3β-ol-BSA. EACH PIG RECEIVED AN INITIAL INJECTION AND TWO BOOSTER INJECTIONS AT 21 DAY INTERVALS.

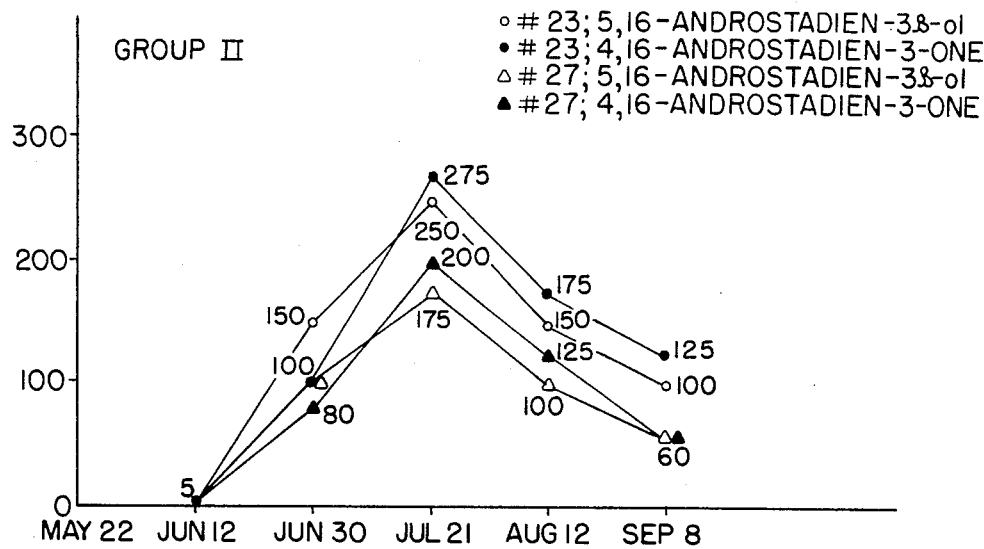
FIG.4 BLOOD TITER LEVELS OF ANTIBODIES TO 5,16-ANDROSTADIEN-3β-ol AND 4,16-ANDROSTADIEN-3-ONE OF FOUR BOARS INJECTED WITH A MIXTURE OF 4mg OF 5,16-ANDROSTADIEN-3β-ol-BSA AND 4mg OF 4,16-ANDROSTADIEN-3-ONE-BSA. THE BOARS IN THIS FEEDING TRIAL EXPERIMENT RECEIVED AN INITIAL INJECTION PLUS TWO BOOSTER INJECTIONS ADMINISTERED AT 21 DAY INTERVALS.
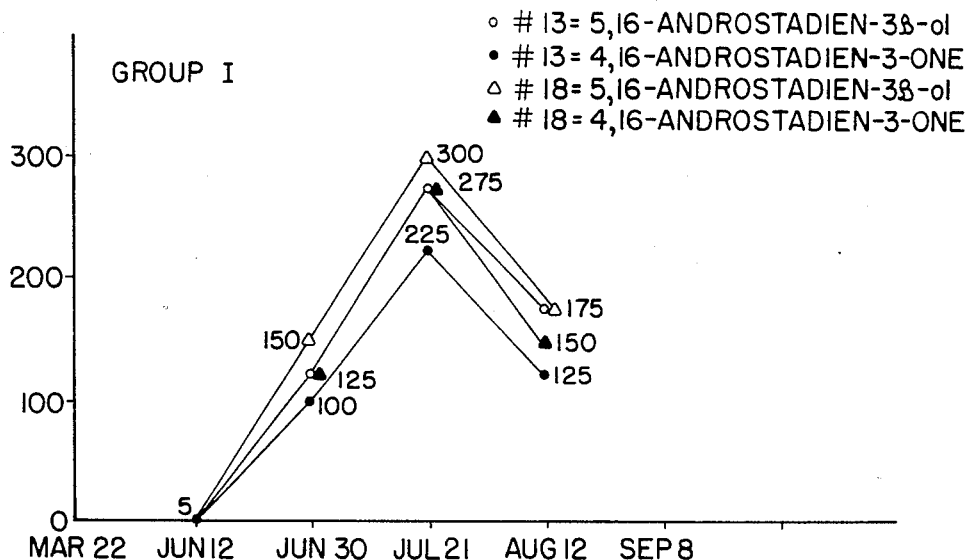

IMMUNOLOGICAL PREVENTION OF BOAR ODOR IN UNCASTRATED MALE PIGS

BACKGROUND OF THE INVENTION

The present invention relates to novel immunogenic compositions which can be employed in a method for eliminating, or at least substantially reducing, the offensive odor associated with uncastrated male pigs and the preparation of meats derived therefrom. These novel immunogens can be characterized as chemical conjugates of certain $C_{19}\Delta^{16}$-steroids bound to a carrier protein and mixtures thereof.

The boar pig possesses a strong characteristic perspiration-like or urine-like odor, called "boar odor" or "boar taint," which is given off particularly upon heating and cooking of the meat. The odor is highly objectionable to consumers and, therefore, carcasses tainted by boar odor are either condemned or subject to restricted usage by USDA meat inspectors.

Since approximately 65% of all boars produce meat which is characterized by this offensive odor, a considerable economic disadvantage is suffered by the swine industry. As elucidated below, the only successful method of preventing boar odor, heretofore, was by castration of young male pigs. However, numerous recent studies on the effects of castration of male pigs which are raised for meat production have clearly shown that rearing uncastrated male pigs presents great economic advantages to the pork producer. Castration is not only a distasteful and labor-intensive chore which retards growth and involves the risk of infection, but it also produces animals with inferior carcass characteristics and a lower feed conversion efficiency (pounds of feed per pounds of weight gain). Rearing young boars to market weights could improve the overall efficiency of lean meat production over castrates by 25-30%.

It is widely accepted that "boar taint" is caused predominantly by the $C_{19}\Delta^{16}$-steroid, 5α-androst-16-en-3-one (5α-androstenone). The steroid is synthesized in the Leydig cells of the testes and is delivered to the blood where it is taken to the adipose tissue and stored in the fat. When needed for sexual stimulation of sows, androstenone is mobilized from the fat and transported by the blood to the salivary glands where it is converted to the reduced alcohol, 5α-androst-16-en-3α-ol. Due to its lypophilic properties, 5α-androstenone and other $C_{19}\Delta^{16}$-steroids are stored in fat at concentrations reaching quantities of micrograms/g of fat. At these concentrations, it is detectable by humans with consumer acceptance depending on the removal of the responsible steroids.

It is also known that the odor associated with these steroids plays an important role in the reproductive behavior of the animal by stimulating sows to assume the mating stance. Before mating, the $C_{19}\Delta^{16}$-steroids are present in the boar's saliva and are transmitted to the female animal, i.e., acting as a pheromone.

Boar taint was investigated for the first time in 1936. Thirty years later, by using the mass spectrometer, R. L. S. Patterson was able to isolate a suspected steroid as the cause of boar taint. Since then, considerable resources have been dedicated to the investigation of the so-called $C_{19}\Delta^{16}$-steroids and their biosynthetic pathways in an effort to eliminate boar taint.

For example, the recent publication by Shenoy, et al. ("The 'boar taint' steroid 5α-androst-16-en-3-one: an immunisation trial," *Acta Endocrinologica*, Vol. 100, pp. 131-136 [1982]) describes an attempt to eliminate boar taint by immunizing uncastrated boars with 5α-androst-16-en-3-one (androstenone) conjugated with bovine thyroglobulin as a carrier protein. This immunization regime did not meet with success since the antibody-bound steroid complex was not removed from the body, and, as it was postulated, having not been recognized by the animal's "feedback" mechanism, actually increased the production of the steroid in the animal.

Further work was done by Williamson and Patterson ("A selective immunization procedure against 5α-androstenone in boars," *Anim. Prod.*, Vol. 35, pp. 353-360 [1982]) wherein a similar procedure selective for boar 5α-androstenone is described. Auto-immunization was effected by the administration of a conjugate of the steroid and bovine serum albumin (BSA). According to these studies, the specific antibody formed sequesters and removes androstenone as it is secreted into the peripheral circulation, thus effectively preventing its transfer to the adipose tissue. However, no results relative to the organoleptic characteristics of the meat from the immunized boars were reported for this protocol.

Earlier, Claus, in the publication entitled, "Neutralization of Pheromones by Antisera in Pigs," *Immunization with Hormones in Reproduction Research*, ed. E. Nieschlag, North-Holland Publishing Co. (1975) described a method of immunizing boars with 3-carboxymethyloximeandrostenone conjugate bound to BSA as a carrier protein. The results, although "encouraging," did not yield a completely satisfactory method for eliminating the taint in boar carcasses.

U.S. Pat. No. 4,384,206 to Bjarno discloses a process for the statistical detection of boar odor by the determination and evaluation of comparative IR-spectrophotometrical transmission data. The reference fails to describe an immunization regime in any manner.

Although methods of immunization to eliminate boar taint are shown by the prior art, each of these methods employ an immunogen only of 5α-androst-16-en-3-one conjugated with a carrier protein. Each of these regimes requires continuous administration and does not effectively eliminate boar taint nor the concomitant accumulation of the boar taint steroid.

SUMMARY OF THE INVENTION

It is, therefore, one object of the present invention to provide a novel immunogen which is effective for the production of certain $C_{19}\Delta^{16}$-steroid specific antibodies in the male pig.

It is another object of this invention to provide a method for the elimination, or at least the substantial reduction, of boar taint.

It is a further object of the present invention to provide a method which inhibits the production and subsequent accumulation of the $C_{19}\Delta^{16}$-steroids in boar carcass fat.

Still another object of this invention is to prevent the biosynthetic production of the $C_{19}\Delta^{16}$-steroids responsible for boar taint.

Another object of the present invention is to provide a vaccine for the immunization of male pigs against the production of $C_{19}\Delta^{16}$-steroids.

A still further object of this invention is to provide an immunogenic composition which is effective for the production of 5,16-androstadien-3β-ol and 4,16-androstadien-3-one specific antibodies in the male pig.

These and other objects are achieved herein by providing an active immunogen consisting of a 5,16-androstadien-3β-ol carrier protein conjugate, a 4,16-androstadien-3-one carrier protein conjugate, or an immunogen mixture of the $C_{19}\Delta^{16}$-steroid carrier protein conjugates which contain at least one of either 5,16-androstadien-3β-ol or 4,16-androstadien-3-one, and any one or more of the other $C_{19}\Delta^{16}$-steroids including 5α-androst-16-en-3-one, 5α-androst-16-en-3β-ol and 5α-androst-16-en-3α-ol. In other words, the present invention contemplates any combination of $C_{19}\Delta^{16}$-steroid carrier protein conjugates, as herein defined, as long as the composition contains either the 5,16-androstadien-3β-ol steroid or the 4,16-androstadien-3-one steroid, or both in the conjugate composition. The immunogenic compositions of this invention can be specifically employed in a method for the elimination, or at least, the substantial and acceptable reduction, of boar taint. Accordingly, the immunogenic composition is administered in any conventional manner, preferably by a vaccine, in an amount and for a time sufficient to effect the production of antibodies specific to the antigenic steroid protein conjugates thereby binding or sequestering these steroids which subsequently accumulate in the boar carcass fat and are primarily responsible for boar taint.

BRIEF DESCRIPTION OF THE DRAWINGS

FIG. 1 is a graphic illustration depicting the body weights and blood titer levels for antibodies to 5,16-androstadien-3β-ol in boars immunized with 4 mg of 5,16-androstadien-3β-ol-BSA.

FIG. 2 is a graphic illustration depicting the blood titer levels of antibodies to 5,16-androstadien-3β-ol in boars immunized with 8, 12 and 16 mg of 5,16-androstadien-3β-ol-BSA, respectively.

FIG. 3 is a graphic illustration depicting the weight gains of boars immunized with 8, 12 and 16 mg of 5,16-androstadien-3β-ol-BSA, respectively.

FIG. 4 is a graphic illustration depicting blood titer levels of antibodies to 5,16-androstadien-3β-ol and 4,16-androstadien-3-one of boars immunized with a mixture of 4 mg of 5,16-androstadien-3β-ol-BSA and 4 mg of 4,16-androstadien-3-one-BSA.

DETAILED DESCRIPTION OF THE INVENTION

In accordance with the present invention, novel immunogenic compositions of the $C_{19}\Delta^{16}$-steroid carrier protein conjugates are employed in a process for the elimination, or at least substantial and organoleptically acceptable reduction, of boar taint which has disadvantageously characterized boar carcass fat and the preparation of all meats prepared from male pigs.

While not wishing to be bound, the autoimmunization technique of this invention is based on the animal's natural defense system, which specifically recognizes and acts against foreign substances in the body. When a foreign compound enters the body, it triggers production of antibodies specific to that substance, which then bind to the invading compound and inactivate it. Compounds, such as steroids, are too small to elicit antibody production, but by chemically linking them to a protein, such as, for example, bovine serum albumin (BSA), which is foreign to the pig, antibodies specific to that particular steroid can be produced. These antibodies will bind to the naturally produced steroids in the blood and remove them from circulation. Through this technique, antibodies can be produced to the $C_{19}\Delta^{16}$-steroids responsible for boar odor, resulting in their removal from circulation before they can accumulate in the animal's fatty tissues.

In accordance with the present invention, it has been surprisingly discovered that the administration of $C_{19}\Delta^{16}$-steroid carrier protein conjugates of 5,16-androstadien-3β-ol and 4,16-androstadien-3-one ($C_{19}\Delta^{16}$-steroid precursors) or mixtures thereof, effectively eliminate, or at least substantially reduce, boar taint. $C_{19}\Delta^{16}$-steroid antibodies specific to these $C_{19}\Delta^{16}$-steroid pathway precursors, as they have been characterized, effectively prevent the accumulation of the boar taint steroids in the fat of the boar. Moreover, it has been determined herein that $C_{19}\Delta^{16}$-steroid conjugate carrier protein mixtures containing at least one of the $C_{19}\Delta^{16}$-steroids 5,16-androstadien-3β-ol or 4,16-androstadien-3-one with any one or more of the other $C_{19}\Delta^{16}$-steroids effectively eliminate the production and accumulation of the boar taint steroids together with the concomitant boar odor.

The present method of immunization, employing conjugates of 5,16-androstadien-3β-ol and 4,16-androstadien-3-one or mixtures thereof (or their mixtures with the other $C_{19}\Delta^{16}$-steroids), has several advantages over conventional techniques which have employed only the 5α-androst-16-en-3-one conjugate. Of particular importance is that the present compositions substantially overcome the feedback phenomenon where the body fails to recognize the steroid-antibody complex resulting in the production of more boar taint steroid (particularly androstenone) by way of the metabolic pathway. The avoidance of this phenomenon results from this immunization scheme which is directed at the precursor steroids in the biosynthetic pathways rather than initiating the immunization procedure only at the 5α-androst-16-en-3-one (androstenone) level thereby "cutting off" the pathways to additional steroid production.

More specifically, the present invention contemplates the preparation of various novel immunogenic compositions. The first is a conjugate of the $C_{19}\Delta^{16}$-steroid 5,16-androstadien-3β-ol and a carrier protein. The second is a conjugate of the $C_{19}\Delta^{16}$-steroid 4,16-androstadien-3-one and a carrier protein. The third is any $C_{19}\Delta^{16}$-steroid mixture including at least one of the precursor $C_{19}\Delta^{16}$-steroids bound to the carrier protein. Any conventional carrier protein may be used to form the $C_{19}\Delta^{16}$-steroid conjugates, such as, for example, BSA and bovine thyroglobulin. Conjugate is defined as a compound formed as a result of the chemical linkage of any $C_{19}\Delta^{16}$-steroid and the carrier proteins. Accordingly, it has been determined herein that the administration of these immunogenic compositions to young boars eliminates, or at least substantially reduces, the accumulation of the $C_{19}\Delta^{16}$-steroids in the carcass fat of the boar and the concomitant offensive odor, i.e., boar taint. This efficacy is facilitated by production of the steroid-specific antibodies which prevent, or at least substantially inhibit, the production of any of the $C_{19}\Delta^{16}$-steroids. It is believed that the antibodies effectively sequester the precursor steroids, i.e., 5,16-androstadien-3β-ol and 4,16-androstadien-3-one, so that none of the boar taint steroids are produced via the biosynthetic pathway. Mixtures with the other $C_{19}\Delta^{16}$-steroids exhibit an added efficacy, apparently by acting more efficiently to block $C_{19}\Delta^{16}$-steroid production via the biosynthetic pathway. As indicated above, precursor steroids are defined as the steroids that are the initial compounds in the biosynthetic pathway shown below.

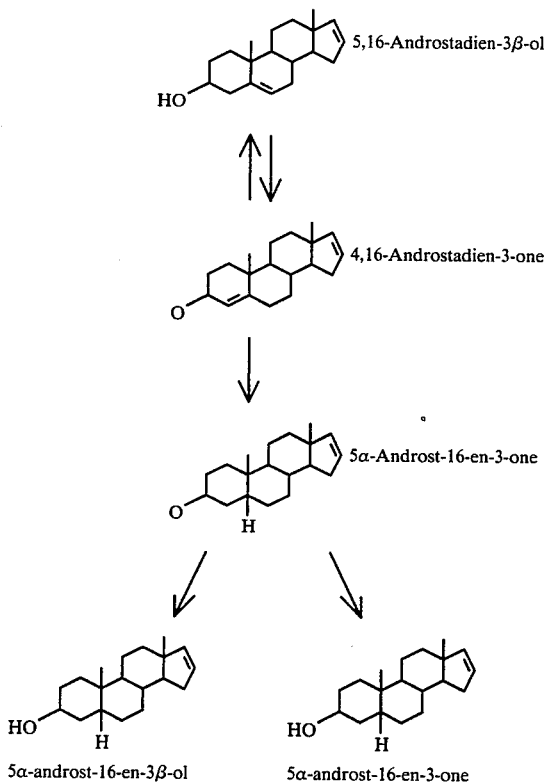

Although it is widely recognized that the accumulation of the $C_{19}\Delta^{16}$-steroid, 5α-androst-16-en-3-one (androstenone) in the carcass fat of the boar is particularly related to the deleterious characteristics of boar odor and boar taste, numerous immunological methods employing androstenone and conventional carrier proteins to produce androstenone-specific antibodies have nevertheless failed to meet with complete success. However, in accordance with the present invention, it has been recognized that since the five $C_{19}\Delta^{16}$-steroids are all believed to contribute to boar taint, to some extent, and inasmuch as each steroid is produced within the same metabolic pathway, the present compositions are directed to producing antibodies that are specific to combinations of the $C_{19}\Delta^{16}$-steroid and particularly to the precursor compounds in the biosynthetic pathway, i.e., 5,16-androstadien-3β-ol and 4,16-androstadien-3-one, thus preventing the biosynthesis of all other subsequent $C_{19}\Delta^{16}$-steroids in the pathway including androstenone. Moreover, these compositions have been surprisingly found to exhibit increased efficacy, i.e., inhibition of boar taint, without compromising the other important factors considered in the marketplace including weight gains, measurements of loin eye area, backfat thickness and percentage of muscle. The rearing of boars rather than barrows, i.e., castrated male pigs, results in the production of approximately 8–10% more lean meat per animal and increases feed efficiency by about 12–15%, thus giving an overall increase of 25–35% efficacy.

The immunogenic compositions of this invention can be administered by deep intramuscular injection in the brachiocephalicus muscle or any other suitable muscle, or by any other conventional method such as, e.g., subcutaneous injection and/or interperitoneal injection. Preferably, these compositions are administered by vaccine composed of a stable water-in-oil emulsion containing milligram quantities of the steroid conjugates to be administered, sterile sodium chloride and Freund's Incomplete Adjuvant in any amount such that a stable oil-in-water emulsion is obtained. For example, 0.4 ml sterile 0.9% sodium chloride and 1.6 ml of Freund's Incomplete Adjuvant is acceptable. Other appropriate diluents, e.g., sterile water, sterile physiological saline and other appropriate adjuvants, can also be substituted for, or used in combination with, Freund's Incomplete Adjuvant, e.g., Freund's Complete Adjuvant, muramyl dipeptide, saponin, colchicine, bestatin, alumina, liposomes, etc. The total amount of each $C_{19}\Delta^{16}$-steroid-BSA conjugate incorporated into the vaccine can vary from as little as 0.5 mg to over 10 mg, e.g., 3.0 mg is an acceptable quantity. The ratio of the $C_{19}\Delta^{16}$-steroid-BSA conjugates can vary from a value of about 1:1, e.g., a ratio of about 1:20 to about 20:1 is acceptable. Pigs can receive multiple injections (usually 2–4) of the vaccine at intervals ranging from 2–4 weeks. The preferred regime is to vaccinate the pigs at 70 to 80 days after birth at a weight of 60–75 lbs. Two booster injections are given at 21 day intervals at weights of 120–130 lbs and 165–175 lbs, respectively.

For a better understanding of the present invention, together with other and further objects, reference is made to the following descriptions and examples.

METHODS

EXAMPLE 1

An immunogen mixture of the $C_{19}\Delta^{16}$-steroid-BSA conjugates of 5,16-androstadien-3β-ol and 4,16-androstadien-3-one, the first two of five boar odor steroids in the pathway were prepared. Thirty-two young boar pigs from eight separate litters were allotted into three different treatment groups. Groups 1 and 2 each consisted of eight intact boar pigs that were immunized on three occasions at average weights of 80, 110 and 150 lbs with the mixtures of $C_{19}\Delta^{16}$-steroid-BSA immunogens. Group 3 consisted of eight intact board pigs that were not immunized and served as an untreated (control) group. The eight pigs in group 4 were castrated at three weeks of age in order to have a barrow group in the study. All pigs were slaughtered when they reached a weight of approximately 240 pounds.

An immunization trial was performed on three boars using a conjugate of 5,16-androstadien-3β-ol. The conjugate was prepared by converting 5,16-androstadien-3β-ol to its hemisuccinate derivative by reacting it with succinic anhydride and pyridine in a steam bath. 5,16-androstadien-3β-ol-hemisuccinate was then reacted with 1-ethyl-3,3'-dimethylaminopropylcarbodiimide in ethanol and distilled water with bovine serum albumin (BSA) to yield 5,16-androstadien-3β-ol-BSA. Each pig was immunized with an initial injection (intramuscular) of 4 mg of the 5,16-androstadien-3β-ol-BSA conjugate. The pigs received a booster injection of the same amount of conjugate 4 weeks later.

Results of this trial are shown in FIG. 1, which represents a comparison of the weight of the animal and its blood titer level for antibodies to 5,16-androstadien-3β-ol. These results are plotted against time.

EXAMPLE 2

An immunization trial was performed on six pigs using a conjugate of 5,16-androstadien-3β-ol. The conjugate was prepared by converting 5,16-androstadien-3- ol to its hemisuccinate derivative by reacting it with succinic anhydride and pyridine in a steam bath. 5,16-androstadien-3β-ol-hemisuccinate was then reacted with 1-ethyl-3,3'-dimethylaminopropylcarbodiimide in ethanol and distilled water with bovine serum albumin (BSA) to yield 5,16-androstadien-3β-ol-BSA. The six pigs were divided into three groups of two, which were immunized with an initial injection (intramuscular) of 8 mg, 12 mg or 16 mg of the 5,16-androstadien-3β-ol-BSA conjugate, respectively. The pigs received 2 booster injections of the same quantity of conjugate at 21 day intervals.

Results of this trial are shown in FIG. 2, which represents a comparison of the blood titer level for antibodies to 5,16-androstadien-3β-ol. These results are plotted against time.

EXAMPLE 3

An immunization trial was performed on six boars using a conjugate of 5,16-androstadien-3β-ol. The conjugate was prepared by converting 5,16-androstadien-3β-ol to its hemisuccinate derivative by reacting it with succinic anhydride and pyridine in a steam bath. 5,16-androstadien-3β-ol-hemisuccinate was then reacted with 1-ethyl-3,3'-dimethylaminopropylcarbodiimide in ethanol and distilled water with bovine serum albumin (BSA) to yield 5,16-androstadien-3β-ol-BSA. The six pigs were divided into three groups of two, which were immunized with an initial injection (intramuscular) of 8 mg, 12 mg or 16 mg of the 5,16-androstadien-3β-ol-BSA conjugate, respectively. The pigs received two booster injections of the same quantity of conjugate at 21 day intervals.

Results of this trial are shown in FIG. 3, which represents the weight gains of the pigs over the length of the trial.

EXAMPLE 4

An immunization trial was performed on forty boars using a conjugate of the mixture of 5,16-androstadien-3β-ol and 4,16-androstadien-3-one. The conjugate of 5,16-androstadien-3β-ol was prepared by converting it to its hemisuccinate derivative by reacting it with succinic anhydride and pyridine in a steam bath. 5,16-androstadien-3β-ol-hemisuccinate was then reacted with 1-ethyl-3,3'-dimethylaminopropylcarbodiimide in ethanol and distilled water with bovine serum albumin (BSA) to yield 5,16-androstadien-3β-ol-BSA. The 4,16-androstadien-3-one was converted to its conjugate by reacting it with O-carboxymethoxylamine hemichloride and dissolving it in pyridine. The mixture was poured in 2N hydrochloric acid and extracted twice with ethyl acetate. The organic extract was washed once with 2N hydrochloric acid and twice with distilled water, and then dried over anhydrous sodium sulfate. Removal of the solvent under vacuum followed by recrystallization from ethyl acetate yielded the $C_{19}\Delta^{16}$-steroid carboxymethoxime. The steroid carboxymethoxime conjugates and tri-N-butylamine were dissolved in p-dioxane and cooled. Isobutyl chloroformate was added, and the solution was stirred for 30 minutes at 4° C. BSA was dissolved in distilled water that had been alkalinated by the addition of sodium hydroxide. After stirring, p-dioxane was then added, and the solution was cooled. The BSA solution was mixed with the original $C_{19}\Delta^{16}$-steroid carboxymethoxime and the resulting solution was stirred for 4 hours. Additional sodium hydroxide was sometimes required to maintain a pH of 7.5. The solution was then dialyzed against running distilled water before being lyophilized.

Two groups of eight pigs were immunized with an initial injection (intramuscular) of 4 mg of the 5,16-androstadien-3β-ol-BSA conjugate and 4 mg of the 4,16-androstadien-3-one-BSA conjugate. The pigs later received two booster injections of the same quantity of the conjugates at 21 day intervals.

Results of this trial are shown in FIG. 4, which represents the blood titer levels of antibodies to 5,16-androstadien-3β-ol and 4,16-androstadien-3-one. These results are plotted over the length of the trial.

RESULTS

The analysis of carcass measurements revealed no difference in loin eye area, backfat thickness or percentage muscle between the immunized boars and the unimmunized boars. Barrows, however, exhibited significantly lower percentage muscle values and higher backfat thickness measurements. Comparison of the daily weight gains and feed conversion data from the four groups revealed no differences between immunized and unimmunized boars (see Table 1 below). Barrows exhibited daily weight gains similar to both immunized and unimmunized boars, but achieved substantially inferior feed efficiency results.

Sensory evaluation of carcass backfat samples for boar odor by a trained panel revealed that immunized boars had significantly lower scores for boar odor than unimmunized boars. However, boar odor scores of the immunized boars were higher than those of the barrows, indicating that the immunological procedure did not result in the absolute elimination of boar odor. Variation in the effectiveness of the immunological procedure on individual pigs was demonstrated by the existence of three immunized boars within Groups 1 and 2 that exhibited boar odor scores comparable to those of the unimmunized boars in Group 3. The reasons for the ineffectiveness of the procedure in these three pigs is not known at this time; however, these pigs appear not to have produced sufficient antibody titers to prevent the accumulation of the $C_{19}\Delta^{16}$-steroids in their fatty tissues when immunized with the $C_{19}\Delta^{16}$-steroid-BSA conjugates.

TABLE 1

| | Blood Titer Levels of Eight Pigs | | | |
| --- | --- | --- | --- | --- |
| | Immunized Boars Group I | Immunized Boars Group II | Control Boars Group III | Unimmunized Boars Group IV |
| Weight Gain (lbs) | | | | |
| No. | 7 | 8 | 7 | 7 |
| Total | 1350 | 1567 | 1378 | 1363 |
| Avg. | 192.9 | 195.9 | 196.9 | 194.7 |
| S.D. | 10.9 | 10.2 | 6.9 | 7.0 |
| Days on Experiment | | | | |
| No. | 7 | 8 | 7 | 7 |

TABLE 1-continued

| Blood Titer Levels of Eight Pigs | | | | |
|---|---|---|---|---|
| | Immunized Boars Group I | Immunized Boars Group II | Control Boars Group III | Unimmunized Boars Group IV |
| Total | 929 | 1077 | 902 | 974 |
| Avg. Daily Gain (lbs) | 1.50 | 1.46 | 1.55 | 1.42 |
| S.D. | 0.27 | 0.08 | 0.21 | 0.17 |
| Total Feed Consumption (lbs) | 3925 | 4574 | 4106 | 4881 |
| Avg. Daily Feed (lbs) | 4.22 | 4.25 | 4.55 | 5.01 |
| Feed/Gain | 2.91 | 2.92 | 2.98 | 3.58 |
| Carcass Measurements | | | | |
| Avg. Live Weight (lbs) | 237.0 | 240.0 | 239.9 | 238.6 |
| Avg. Hot Carcass Weight (lbs) | 170.9 | 169.6 | 168.1 | 173.0 |
| Avg. Loin Eye Area (in$^2$) | 4.70 | 4.81 | 4.46 | 4.35 |
| Avg. Backfat (mm) | 19.7 | 20.3 | 22.0 | 34.7 |
| Avg. Carcass Muscle (lbs) | 93.9 | 93.7 | 90.5 | 87.7 |
| Avg. % Muscle | 55.0 | 55.3 | 53.9 | 50.1 |

Thus, while the invention has been described with reference to certain preferred embodiments, those skilled in the art will realize that changes and modifications may be made thereto without departing from the full and intended scope of the appended claims:

What is claimed is:

1. An immunogenic composition for the elimination of boar taint comprising a $C_{19}\Delta^{16}$-steroid conjugate and a carrier protein, wherein the $C_{19}\Delta^{16}$-steroid is 5,16-androstadien-3$\beta$-ol, 4,16-androstadien-3-one and mixtures thereof.

2. An immunogenic composition of claim 1, wherein at least one of said $C_{19}\Delta^{16}$-steroid conjugates and a carrier protein is mixed with 5$\alpha$-androst-16-en-3-one, 5$\alpha$-androst-16-en-3$\alpha$-ol, 5$\alpha$-androst-16-en-3$\beta$-ol and mixtures thereof.

3. An immunogenic composition of claim 1, wherein said carrier protein is bovine serum albumin or bovine thyroglobulin.

4. An immunogenic composition of claim 1, wherein the ratio of said $C_{19}\Delta^{16}$-steroid conjugate mixtures is equal.

5. An immunogenic composition of claim 2, wherein the ratio of $C_{19}\Delta^{16}$-steroid conjugate mixtures is equal.

6. A vaccine containing the composition of claim 1 and a pharmaceutically acceptable carrier.

7. A vaccine containing the composition of claim 2 and a pharmaceutically acceptable carrier.

8. A vaccine of claim 6, wherein said pharmaceutically acceptable carrier is a water-in-oil emulsion containing sodium chloride and Freund's Incomplete Adjuvant.

9. A vaccine of claim 7, wherein said pharmaceutically acceptable carrier is a water-in-oil emulsion containing sodium chloride and Freund's Incomplete Adjuvant.

10. A vaccine of claim 8, wherein said $C_{19}\Delta^{16}$-steroid conjugate or mixtures thereof are present in a total quantity ranging from 0.5 mg to 10 mg.

11. A vaccine of claim 9, wherein said $C_{19}\Delta^{16}$-steroid conjugate or mixtures thereof are present in a total quantity ranging from 0.5 mg to 10 mg.

12. A method for the immunization of male pigs against boar taint comprising the administration of an immunogenic composition containing a $C_{19}\Delta^{16}$-steroid conjugate to a carrier protein, wherein the $C_{19}\Delta^{16}$-steroid is 5,16-androstadien-3$\beta$-ol, 4,16-androstadien-3-one and mixtures thereof, said composition being administered in an amount and for a time sufficient to effect the production of said $C_{19}\Delta^{16}$-steroid specific antibodies thereby eliminating or substantially reducing boar taint.

13. A method of claim 12, wherein at least one of said $C_{19}\Delta^{16}$-steroid conjugate and a carrier protein is mixed with 5$\alpha$-androst-16-en-3-one, 5$\alpha$-androst-16-en-3$\alpha$-ol, 5$\alpha$-androst-16-en-3$\beta$-ol and mixtures thereof.

14. A method of claim 12, wherein said protein carrier is bovine serum albumin or bovine thyroglobulin.

15. A method of claim 12, wherein the ratio of said $C_{19}\Delta^{16}$-steroid mixtures is equal.

16. A method of claim 13, wherein the ratio of said $C_{19}\Delta^{16}$-steroid mixtures is equal.

* * * * *